United States Patent [19]

Philippe et al.

[11] Patent Number: 5,693,670

[45] Date of Patent: Dec. 2, 1997

[54] COMPOSITION CONTAINING A DIHYDROXYACETONE PRECURSOR

[75] Inventors: Michel Philippe, Wissous; Remy Tuloup; Armelle de Salvert, both of Paris; Daniel Sera, L'Hay Les Roses; Pierre Fodor, Garches, all of France

[73] Assignee: L'Oreal, Paris, France

[21] Appl. No.: 534,314

[22] Filed: Sep. 27, 1995

[30] Foreign Application Priority Data

Oct. 24, 1994 [FR] France ............................ 94 12686

[51] Int. Cl.⁶ ........................ A61K 31/235; A61K 31/12
[52] U.S. Cl. ............................ 514/545; 514/675
[58] Field of Search .......................... 514/675, 545

[56] References Cited

FOREIGN PATENT DOCUMENTS

| | | |
|---|---|---|
| 0 547 864 | 6/1993 | European Pat. Off. . |
| 94 04130 | 3/1994 | WIPO . |
| 94 13258 | 6/1994 | WIPO . |
| 94 22419 | 10/1994 | WIPO . |

OTHER PUBLICATIONS

J. Soc. Cosmet. Chem, 35, 265–272 (Aug. 1984). Robin et al.

*Primary Examiner*—Zohreh Fay
*Attorney, Agent, or Firm*—Oblon, Spivak, McClelland, Maier & Neustadt, P.C.

[57] ABSTRACT

The invention relates to a composition, which may be cosmetic or dermatological, Containing at least one dihydroxyacetone precursor. The invention also relates to a composition, which may be cosmetic or dermatological, containing at least one dihydroxyacetone precursor and a compound capable of converting this precursor into dihydroxyacetone. Finally, the invention relates to such a composition packaged in a specific manner and to the use of the composition for artificial tanning of the skin.

21 Claims, No Drawings

COMPOSITION CONTAINING A DIHYDROXYACETONE PRECURSOR

BACKGROUND OF THE INVENTION

1. Field of the Invention

The invention relates to a cosmetic or dermatological composition containing at least one precursor of a substance whose active form is sought for its cosmetic activity. One of the applications of the invention relates to compositions capable of rapidly imparting to the skin a color similar to that obtained on prolonged exposure to ultraviolet, solar or artificial radiation, while at the same time avoiding the drawbacks of such an exposure (erythema, burning, loss of elasticity, appearance of wrinkles, premature ageing of the skin, and the like).

2. Description of Related Art

For many years, the prior art has taught of the involvement of dihydroxyacetone (DHA hereinafter in the text) in the artificial coloring of the skin (Bobin et al., J. Soc. Cosmet. Chem., 35 pages 265–272, 1984). DHA reacts with the amino acids naturally contained in the lipid film of the stratum corneum, and forms melanoids via a Maillard reaction (Maillard L. C., C. R. Acad. Sci. 154, 66–68, 1912).

Cosmetic compositions used for the purpose of artificially coloring the skin and containing DHA are widely described in the prior art, such as, for example, in the Patent Application FR-A-2,597,345 by the Applicant.

In order to improve the effects of DHA, it is often combined with other substances for the purpose of increasing the speed of appearance of the color or the resistance of the latter over time. The combinations described in applications WO-A-9404130 or EP-A-547,864 may be mentioned, for example.

The use of DHA has a number of drawbacks which are quite incompatible with customer appeal. Indeed, the stability of DHA in formulation is entirely relative, causing degradation of the compound over time. It is observed in particular that compositions containing DHA sometimes acquire, before use, a color which users find quite unpleasant. In addition, a nauseating and unpleasant odor which consumers generally find undesirable may develop over time with these same compositions. The pH of the composition also decreases over time, which in the long run makes the composition incompatible with use in topical application.

Moreover, taking only the activity of DHA into consideration, it is known that its remanence on the skin is not perfect.

SUMMARY OF THE INVENTION

In order to solve these drawbacks, the Applicant proposes a novel cosmetic composition, one of the aims of which is to provide DHA at the time of application of the latter, in particular to the skin, without, however, the said composition containing DHA as such.

Thus, a first object of the invention relates to a cosmetic or dermatological composition comprising at least one DHA precursor.

It has been found that a cosmetic or dermatological composition containing, in a cosmetically or dermatologically acceptable vehicle, at least one esterified dihydroxyacetone derivative corresponding to the general formula:

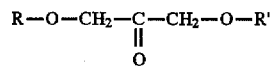

in which R and R' represent a hydrogen atom or a saturated or unsaturated, linear, branched or cyclic, optionally hydroxylated acyl radical having from 2 to 25 carbon atoms, it being possible for R and R' to be identical or different on condition that they are never simultaneously a hydrogen atom.

R and R' are preferably a benzoyl radical or an alkylbenzoyl radical or an acylbenzoyl radical or a 2-hydroxy-2-phenylacetyl radical, which is optionally hydroxylated.

DESCRIPTION OF THE PREFERRED EMBODIMENTS

The invention as described above makes it possible to improve the remanence of the product applied as well as its stability in formulation. It nevertheless retains that one of the main advantages sought for such a cosmetic or dermatological composition, namely to use DHA for its properties, can only be achieved if the esterified derivative is converted into DHA at the moment of application. Such a hydrolysis, which at the moment of application releases DHA, is only possible in the presence of one (or more) compounds capable of cleaving the ester bond(s) of the derivative. Such compounds are found on the skin. However, in order to improve the effectiveness of the composition according to the invention, it is desirable simultaneously to provide the esterified DHA derivative and the compound capable of cleaving an ester bond.

Thus, a second object of the invention relates to a composition comprising at least one esterified dihydroxyacetone derivative corresponding to the general formula:

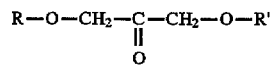

in which R and R' represent a hydrogen atom or a saturated or unsaturated, linear, branched or cyclic, optionally hydroxylated acyl radical having from 2 to 25 carbon atoms, it being possible for R and R' to be identical or different on condition that they are never simultaneously a hydrogen atom, and at least one compound capable of cleaving at least one ester bond.

R and R' are preferably a benzoyl radical or an alkylbenzoyl radical or an acylbenzoyl radical or a 2-hydroxy-2-phenylacetyl radical, which is optionally hydroxylated.

This composition may advantageously be in a cosmetically or dermatologically acceptable form, for the purpose of its use in the fields in question.

According to a preferred embodiment of the invention, the acyl radical has from 3 to 18 carbon atoms.

The esterified derivative may advantageously be chosen from the group consisting of:

2-oxopropyl 1,3-didodecanoate, 2-oxopropyl 1,3-dihexadecanoate, 2-oxopropyl 3-hexadecanoate.

According to a preferred embodiment of the invention, the esterified derivative may be at a concentration ranging from 0.1% to 20% and preferably at a concentration ranging from 0.5% to 10%.

Here and in the remainder of the text, the percentages are given by weight relative to the total weight of the composition.

According to the second object of the invention, and in a particular embodiment of the latter, the compound capable of cleaving at least one ester bond may be any nucleophilic compound acceptable in cosmetics. Thus, alcohols, thiols, amines or anions may be mentioned.

Among the amines, a hydroxylated amine such as, for example, 3-amino-1,2-propanediol, 2-amino-2-methyl-1,3-propanediol, 2-amino-2-methylpropanol, 2-amino-2-hydroxymethyl-1,3-propanediol, glucamine or N-methylglucamine, or an amino acid such as, for example, lysine, arginine or histidine, will preferably be chosen.

Among the anions, a carboxylate anion such as, for example, fatty acid salts, amino acid salts or lipoamino acid salts will preferably be chosen.

Enzymes are the second large family of compounds which are capable of cleaving at least one ester bond and which may be used in the invention. Examples which may be mentioned are hydrolases, among which there will be mentioned, in a non-limiting manner, lipases, esterases or proteases. In the lipases, a pig pancreatic lipase such as that sold under the name Type II by the company Sigma or alternatively lipolase SP 644 sold by the company Novo-Nordisk will preferably be chosen.

According to the second object of the invention, and in another particular embodiment of the latter, the compound capable of cleaving at least one ester bond may be used at a concentration ranging from 0.1% to 30% and preferably ranging from 0.5% to 15%.

It is, however, preferable in the common use of such compositions to arrange matters such that hydrolysis of the esterified DHA derivative takes place only at the moment of application of the compositions. It is thus advantageous to provide packaging such that the esterified derivative and the compound capable of cleaving at least one ester bond are packaged so as not to be in contact with each other.

A third object of the invention thus relates to a composition in which the esterified derivative and the compound capable of cleaving at least one bond may be packaged so as not to be in contact with each other.

The two separate compartments joined together may, for example, constitute a single packaging in the form of a flexible tube, such that the esterified derivative and the compound capable of cleaving at least one ester bond are mixed together only when each of them is expelled from its own compartment. This expulsion may or may not be simultaneous. Mixing will take place during application.

Another form of packaging with two separate compartments joined together may be such that the esterified derivative or the compound capable of cleaving an ester bond is encapsulated in the form of microcapsules, spherules or any other form known to those skilled in the art, and is packaged in the presence of the other component of the invention in a different form, which is itself known to those skilled in the art.

In a cosmetic or dermatological form of this packaging, the non-encapsulated part of the invention may be a cream, a gel or any other form known to those skilled in the art.

There is nothing to prevent the two components from each being encapsulated. Here also, those skilled in the art know how to prepare such forms.

The release will take place during application, by crushing of the capsules under pressure exerted by the user, and the compositions thus released will be mixed together.

Regardless of the embodiment of the invention, in a cosmetic or dermatological application, it may also contain any other cosmetically or dermatologically acceptable constituent usually used in this type of composition, and in particular additives used to increase the effectiveness of the DHA originating from hydrolysis of the derivative.

The cosmetic or dermatological composition according to any one of the embodiments of the invention and, in particular, the separate compositions respectively containing the esterified derivative and the compound, may be provided as an oil, a gel, an emulsion or a vesicle dispersion.

A fourth subject of the invention relates to the use of these cosmetic or dermatological compositions for the purpose of artificially coloring the skin.

A fifth subject of the invention relates to a process for the artificial coloring of the skin using, by application, a composition as described above in the text.

Having generally described this invention, a further understanding can be obtained by reference to certain specific examples which are provided herein for purposes of illustration only and are not intended to be limiting unless otherwise specified.

Examples of compositions according to the invention will now be given in a non-limiting manner.

EXAMPLE 1

Self-tanning suncream

A. Emulsion containing the dihydroxyacetone ester:

| Oily phase: | |
| --- | --- |
| Steareth-2 (surfactant) | 3% |
| Steareth-21 (surfactant) | 2% |
| PPG-15 stearyl ether (surfactant) | 29.5% |
| Dihydroxyacetone palmitate | 14.6% |
| Aqueous phase: | |
| Phenoxyethanol (preserving agent) | 0.5% |
| Water | qs 100% |

B. Emulsion containing lipase:

| Oily phase: | |
| --- | --- |
| Steareth-2 (surfactant) | 3% |
| Steareth-21 (surfactant) | 2% |
| PPG-15 stearyl ether (surfactant) | 29.5% |
| Aqueous phase: | |
| Phenoxyethanol (preserving agent) | 0.5% |
| Lipase SP644 | 2% |
| Water | qs 100% |

Emulsions A and B are placed in two separate compartments and mixed together at the moment of application to the skin.

After application to the skin, the product obtained gives the skin a progressively tanned coloration.

EXAMPLE 2

Self-tanning suncream

A. Emulsion containing the dihydroxyacetone ester:

| Oily phase: | |
| --- | --- |
| Steareth-2 (surfactant) | 3% |
| Steareth-21 (surfactant) | 2% |
| PPG-15 stearyl ether (surfactant) | 29.5% |

-continued

| | |
|---|---|
| Dihydroxyacetone laurate | 10% |
| Aqueous phase: | |
| Phenoxyethanol (preserving agent) | 0.5% |
| Water | qs 100% |
| B. Emulsion containing lipase: | |
| Oily phase: | |
| Steareth-2 (surfactant) | 3% |
| Steareth-21 (surfactant) | 2% |
| PPG-15 stearyl ether (surfactant) | 29.5% |
| Aqueous phase: | |
| Phenoxyethanol (preserving agent) | 0.5% |
| Lipase 100 L | 1% |
| Water | qs 100% |

The emulsions are placed in two different compartments and are brought into contact at the moment of application.

EXAMPLE 3

Self-tanning suncream

A. Emulsion containing the dihydroxyacetone ester:

| | |
|---|---|
| Oily phase: | |
| Steareth-2 (surfactant) | 3% |
| Steareth-21 (surfactant) | 2% |
| PPG-15 stearyl ether (surfactant) | 29.5% |
| Dihydroxyacetone palmitate | 14.6% |
| Aqueous phase: | |
| Phenoxyethanol (preserving agent) | 0.5% |
| Water | qs 100% |
| B. Emulsion containing lysine: | |
| Oily phase: | |
| Steareth-2 (surfactant) | 3% |
| Steareth-21 (surfactant) | 2% |
| PPG-15 stearyl ether (surfactant) | 12% |
| Cetyl alcohol | 3.5% |
| Petrolatum | 5% |
| Aqueous phase: | |
| Gycerol | 6% |
| Phenoxyethanol (preserving agent) | 0.5% |
| Lysine | 5% |
| Water | qs 100% |

Emulsions A and B are placed in two separate compartments and mixed together at the moment of application to the skin.

After application to the skin, the product obtained gives the skin a progressively tanned coloration.

EXAMPLE 4

Self-tanning suncream

A. Emulsion containing the dihydroxyacetone ester:

| | |
|---|---|
| Oily phase: | |
| Steareth-2 (surfactant) | 3% |
| Steareth-21 (surfactant) | 2% |
| PPG-15 stearyl ether (surfactant) | 29.5% |
| Dihydroxyacetone laurate | 10% |
| Aqueous phase: | |
| Phenoxyethanol (preserving agent) | 0.5% |
| Water | qs 100% |
| B. Emulsion containing lysine: | |
| Oily phase: | |
| Steareth-2 (surfactant) | 3% |
| Steareth-21 (surfactant) | 2% |
| PPG-15 stearyl ether (surfactant) | 12% |
| Cetyl alcohol | 3.5% |
| Petrolatum | 5% |
| Aqueous phase: | |
| Gycerol | 6% |
| Phenoxyethanol (preserving agent) | 0.5% |
| Lysine | 5% |
| Water | qs 100% |

The emulsions are placed in two different compartments and are brought into contact at the moment of application.

Although the present invention has been described with reference to specific details of certain embodiments thereof, it is not intended that such details should be regarded as limitations upon the scope of the invention except insofar as they are included in the accompanying claims.

What is claimed as new and desired to be secured by Letters Patent of the United States is:

1. A cosmetic or dermatological composition comprising, in a cosmetically or dermatologically acceptable vehicle, at least one esterified dihydroxyacetone derivative corresponding to the general formula:

$$R-O-CH_2-\underset{\underset{O}{\|}}{C}-CH_2-O-R'$$

wherein R and R' represent a hydrogen atom or a saturated or unsaturated, linear, branched or cyclic acyl radical having from 2 to 25 carbon atoms, and where R and R' are identical or different on condition that they are never simultaneously a hydrogen atom.

2. A composition comprising at least one esterified dihydroxyacetone derivative corresponding to the general formula:

$$R-O-CH_2-\underset{\underset{O}{\|}}{C}-CH_2-O-R'$$

where R and R' represent a hydrogen atom or a saturated or unsaturated, linear, branched or cyclic acyl radical having from 2 to 25 carbon atoms, and where R and R' are identical or different on condition that they are never simultaneously a hydrogen atom, and further containing at least one compound capable of cleaving at least one ester bond.

3. The composition according to claim 1, in which said acyl radical is a benzoyl radical, an alkylbenzoyl radical, an acylbenzoyl radical or a 2-hydroxy-2-phenylacetyl radical.

4. The composition according to claim 1, in which said acyl radical is hydroxylated.

5. The composition according to claim 1, in which said acyl radical has from 3 to 18 carbon atoms.

6. The composition according to claim 1, in which said esterified derivative is selected from the group consisting of 2-oxopropyl 1,3-didodecanoate, 2-oxopropyl 1,3-dihexadecanoate and 2-oxopropyl 3-hexadecanoate.

7. The composition according to claim 1, in which said esterified derivative is at a concentration ranging from 0.1% to 20% by weight relative to the total weight of the composition.

8. The composition according to claim 1, in which said esterified derivative is at a concentration ranging from 0.5% to 10% by weight relative to the total weight of the composition.

9. The composition according to claim 2, in which said compound capable of cleaving at least one ester bond is a nucleophilic compound.

10. The composition according to claim 2, in which said compound capable of cleaving at least one ester bond is an amine, an anion, or an enzyme.

11. The composition according to claim 2, in which said compound capable of cleaving at least one ester bond is a hydroxylated amine, a carboxylate anion or a hydrolase.

12. The composition according to claim 2, in which said compound capable of cleaving at least one ester bond is selected from the group consisting of 3-amino-1,2-propanediol, 2-amino-2-methyl-1,3-propanediol, 2-amino-2-methylpropanol, 2-amino-2-hydroxymethyl-1,3-propanediol, glucamine or N-methylglucamine, a lysine, arginine, and a histidine.

13. The composition according to claim 2, in which said compound capable of cleaving at least one ester bond is a lipase, an esterase or a protease.

14. The composition according to claim 2, in which said compound capable of cleaving at least one ester bond is a lipase.

15. The composition according to claim 2, in which said compound capable of cleaving at least one ester bond is at a concentration ranging from 0.1% to 30% by weight relative to the total weight of the composition.

16. The composition according to claim 2, in which said compound capable of cleaving at least one ester bond is at a concentration ranging from 0.5% to 15% by weight relative to the total weight of the composition.

17. The composition according to claim 2, in which said esterified derivative and said compound capable of cleaving at least one ester bond are packaged so as not to be in contact with each other.

18. The composition according to claim 17, in which said esterified derivative and said compound capable of cleaving at least one ester bond are contained in a single packaging with two compartments.

19. The composition according to claim 18, in which at least one from among the esterified derivatives and said compound capable of cleaving at least one bond is encapsulated.

20. The composition according to claim 1, characterized in that it consists of a composition for artificially coloring the skin.

21. A method for coloring the skin, consisting in applying thereto a composition according to claim 1.

* * * * *